United States Patent [19]

Chervitz et al.

[11] Patent Number: 5,665,110
[45] Date of Patent: Sep. 9, 1997

[54] SUTURE ANCHOR SYSTEM AND METHOD

[75] Inventors: Alan Chervitz; E. Marlowe Goble, both of Logan, Utah

[73] Assignee: MedicineLodge, Inc., Logan, Utah

[21] Appl. No.: 531,780

[22] Filed: Sep. 21, 1995

[51] Int. Cl.$^6$ ................................................ A61B 17/00
[52] U.S. Cl. .................................. 606/232; 128/898
[58] Field of Search .............................. 606/232, 104, 606/73, 75, 187, 60, 92–95; 623/13; 433/228.1, 48; 523/116

[56] References Cited

U.S. PATENT DOCUMENTS

| | | |
|---|---|---|
| Re. 34,293 | 6/1993 | Goble et al. . |
| 4,263,913 | 4/1981 | Malmin .................... 606/187 |
| 4,632,100 | 12/1986 | Somers et al. . |
| 4,696,301 | 9/1987 | Barabe ...................... 606/216 |
| 4,738,255 | 4/1988 | Goble et al. . |
| 4,772,286 | 9/1988 | Goble et al. . |
| 4,779,616 | 10/1988 | Johnson . |
| 4,870,957 | 10/1989 | Goble et al. . |
| 4,927,421 | 5/1990 | Goble et al. . |
| 4,946,468 | 8/1990 | Li . |
| 4,997,433 | 3/1991 | Goble et al. . |
| 5,013,316 | 5/1991 | Goble et al. . |
| 5,071,420 | 12/1991 | Paulos et al. . |
| 5,100,417 | 3/1992 | Cerier et al. . |
| 5,102,421 | 4/1992 | Anspach, Jr. . |
| 5,129,902 | 7/1992 | Goble et al. . |
| 5,139,520 | 8/1992 | Rosenberg . |
| 5,141,520 | 8/1992 | Goble et al. . |
| 5,192,283 | 3/1993 | Ling et al. .................. 606/92 |
| 5,207,679 | 5/1993 | Li . |
| 5,211,650 | 5/1993 | Noda . |
| 5,224,946 | 7/1993 | Hayhurst et al. . |
| 5,236,445 | 8/1993 | Hayhurst et al. . |
| 5,258,016 | 11/1993 | DiPoto et al. . |
| 5,352,229 | 10/1994 | Goble et al. . |
| 5,411,506 | 5/1995 | Goble et al. . |
| 5,411,523 | 5/1995 | Goble . |
| 5,454,811 | 10/1995 | Huebner ...................... 606/73 |

Primary Examiner—Jeffrey A. Schmidt
Attorney, Agent, or Firm—M. Reid Russell

[57] ABSTRACT

A suture anchor system and procedure for securing a suture, into to extend from a bone cortex surface. The system includes forming a hole into a bone cortex surface that is of a diameter and depth to provide a wall surface area that is at least as great as the surface area of an end section of a suture or sutures fitted therein, and, by filling the hole with an adhesive that is allowed to cure, a suture mounting is provided that will have a pullout strength or purchase that is greater than a load as is anticipated to be applied thereto when the suture is used to connect a ligament, or the like, to the bone. To increase which purchase a portion of the hole formed into the bone cortex may be counter bored to form an outwardly extending shirt area to increase the hole wall surface area, the suture may be folded upon itself and the fold fitted into the formed hole, a knot may be tied in the suture end, or a pair or more of sutures can be combined together that can also be folded and a knot tied therein, for increasing the area of the suture that is for fitting in the formed hole. Which hole containing the suture or sutures is then filled with an adhesive material, that, when cured, completes the suture mounting to the bone cortex. The invention further includes the steps for practicing the suture mounting system.

5 Claims, 4 Drawing Sheets

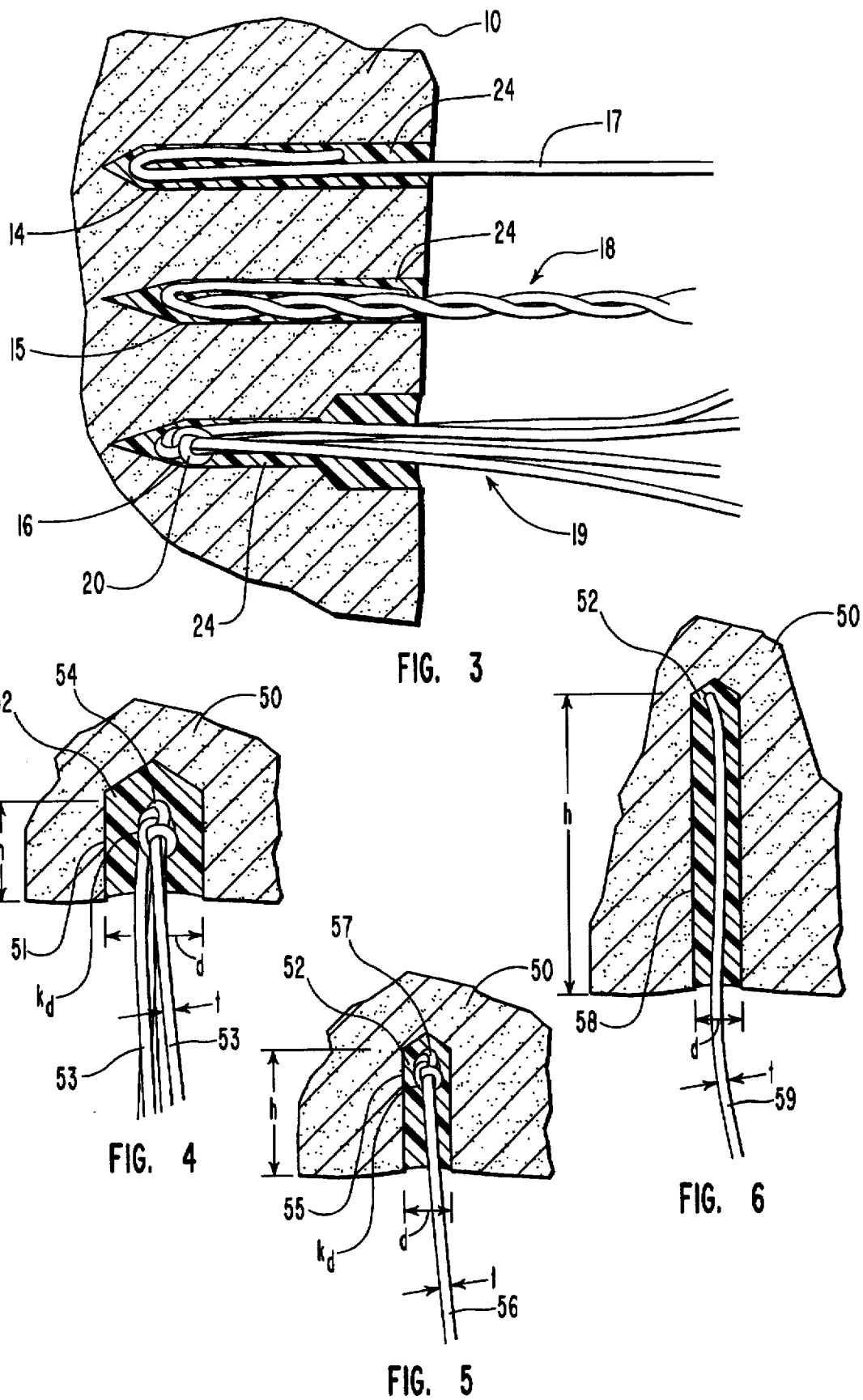

SUTURE ANCHOR SYSTEM AND METHOD

BACKGROUND OF THE INVENTION

1. Field of the Invention

This invention relates to medical equipment and in particular to devices and methods for securing a suture to a bone for use in maintaining a section of a ligament or soft tissue thereto.

2. Prior Art

Devices and methods for positioning and securing an anchor, fastener or the like to a bone to secure a suture thereto that is used to fasten a section of a ligament, or the like, are well known. A number of earlier inventions of one or both of the present inventors show several different suture anchor arrangements and drivers. For example, one such a driver mounting a suture anchor wherefrom a suture extends that is for turning the anchor into a bone is shown in a U.S. Patent to E. Marlowe Goble, U.S. Pat. No. 4,632,100. Also, other driver and suture anchor combinations of one or both of the present inventors, U.S. Pat. Nos. 5,411,506 and 5,411,523, have provided for turning an anchor whereto a suture is connected into a bone for use in mounting a ligament, or the like, to that bone. Further, other patents to one of the present inventors, U.S. Pat. Nos. 4,738,255, 5,013,316 and 5,141,520, illustrate other driver and anchor combinations and ligament mounting arrangements are shown in U.S. Pat. Nos. 4,772,286 and Re. 34,293, 4,870, 957, 4,927,421, 4,997,433, 5,129,902, 5,352,229. Unlike these earlier suture anchor and driver combinations, however, the present invention provides for seating and mounting a suture directly into a hole drilled or otherwise formed into a bone without a need to use a separate anchor or driver.

A number of combinations of anchors, some of which include arrangements for capturing, maintaining and fitting sutures to extend from seated anchors are shown in U.S. Patents issued to others, Nos. 4,779,616; 4,946,468; 5,071, 420; 5,100,417; 5,102,421; 5,139,520; 5,207,679; 5,211, 650; 5,224,946; 5,236,445; and 5,258,016. None of these patents, however, provide for a direct mounting of a suture into a bone material that are like the arrangement of the invention that provides a simple and easily practiced system and process for rapidly and reliably mounting a suture to a location on or into a bone surface.

SUMMARY OF THE INVENTION

It is therefore a principal object of the present invention in a suture anchor system and procedure to provide for mounting a suture to a selected location in a bone cortex for connecting a ligament, or the like, thereto.

Another object of the present invention is to provide a suture anchor system that can be a single suture strand, or multiple suture strands and with or without a knot formed in the end thereof, with the suture strand or strands end for fitting in a hole that has been formed into a bone to receive an adhesive to encapsulate the suture or sutures end within the hole, mounting it therein.

Another object of the present invention is to provide a suture anchor system that may be a single suture or multiple sutures that are wound, braided, or otherwise maintained together, for fitting into a hole that is formed into a bone cortex so as to provide a hole wall area and depth relationship to the suture or sutures cross section and length of a suture section for fitting into and bond in which hole when the hole is filled with a particular adhesive.

Another object of the present invention is to provide for filling the formed hole with the adhesive that will, when cured, encapsulate the suture or sutures therein, bonding to the hole wall and suture or sutures to permanently mount the suture or sutures therein, with portion or portions of the suture or sutures extending from the bone surface for attachment to a ligament, or the like.

Another object of the present invention is to provide a suture anchor system that, to increase pullout strength of an anchored suture, a single suture or plurality of sutures ends that are for fitting into the bone hole are knotted and receive an adhesive in that bone hole that, when dried, bonds to both the hole wall and knotted suture or sutures, the knot or knots to add additional pullout strength over a suture or sutures without such knotted end.

Still another object of the present invention is to provide a suture anchor system where, to increase pullout strength of an anchored suture, the bone hole is formed to have an outwardly sloping skirt portion, increasing the hole interior surface area.

Still another object of the present invention is to provide a process for securing a suture or sutures to a bone cortex where a hole is drilled into a bone material that is of a determined width and depth to receive an end portion a suture or sutures fitted therein and receive an adhesive to encapsulate the suture or sutures end portion or portions and bond thereto and to the bone hole wall surface prohibiting the suture or sutures end portion or portions from being pulled therefrom when an anticipated or greater tensile force is applied to the suture or sutures.

Still another object of the present invention is to provide a suture or sutures end portion or portions mounting that is simple and reliable to use for mounting a suture or sutures to a bone cortex surface, with the suture or sutures then used for attaching to a ligament, or the like.

In accordance with the above objects, the present invention is in a suture anchor system and process for mounting a suture or sutures into, so as to extend from, a bone material surface for attachment to a ligament, or the like. The system includes a single suture or a number of sutures that may be wound, braided, or otherwise maintained together, with an end portion or portions of the suture or sutures for fitting into a hole that has been formed through a bone cortex surface and into the bone material. The hole is formed to have a diameter and depth such that, with the suture or sutures end portion or portions fitted therein, and with an introduction of an adhesive or resin therein, and after adhesive or resin drying, curing or polymerizing, the suture end portion or portions will be secured within the hole, resisting withdrawal when a tensile stress is applied thereto. The suture or sutures end portion or portions can be knotted and fitted within the prepared hole to increase suture surface area, producing a greater purchase.

In practice, a bone hole diameter and depth are selected for the material of the bone whereto the suture or sutures are to be attached, taking into account the suture or sutures portion or portions length as will be fitted in the hole and thickness and whether the suture or sutures end portion or portions are knotted, and considering the adhesive to be used. In practice, an adhesive known as polymethlymethacrylate (PMMA), similar to that manufactured by Howmedica, Richards or Zimmer USA, that will dry within approximately one to twenty minutes has been used. Further, a light activate resin as commonly used by dentists can be used as the adhesive for this invention.

The pullout strength or purchase of the mounted suture or sutures that is the resistance to the suture or sutures being pulled out of the mount can be increased when the suture or sutures end or ends has been knotted. A hole of the invention formed into a bone mass should have a hole wall surface area that is at least equal to the suture or sutures thickness and length of the suture portion that is for positioning in the hole. In practice, this purchase should be the tensile strength of the suture or sutures mounted in the hole.

With the single suture or plurality of sutures end or ends adhesively mounted within the bone hole, the suture or sutures can be used to tie a ligament, or the like, onto that bone surface.

BRIEF DESCRIPTION OF THE DRAWINGS

These and other objects and features of the invention will become more fully apparent from the following description, in which the invention is described in detail in conjunction with the accompanying drawings. In which drawings:

FIG. 3 is a view like that of FIG. 2, showing the formed holes with the tools removed and an adhesive filling the individual holes;

FIG. 4 is a side elevation view of a section of bone material with a shallow broad hole formed therein that a knotted section or portion of a pair of sutures has been fitted into, with the hole shown filled with an adhesive;

FIG. 5 is a side elevation view of a section of bone material showing a deep narrow hole formed therein wherein a knotted end portion of a single suture has been positioned and showing the hole filled with an adhesive;

FIG. 6 is a side elevation view of a section of bone material wherein a narrow hole has been formed that is deeper than the hole of FIG. 5, and contains a straight end section or portion of a single suture fitted therein and showing the hole filled with an adhesive;

DETAILED DESCRIPTION

Figure 1:
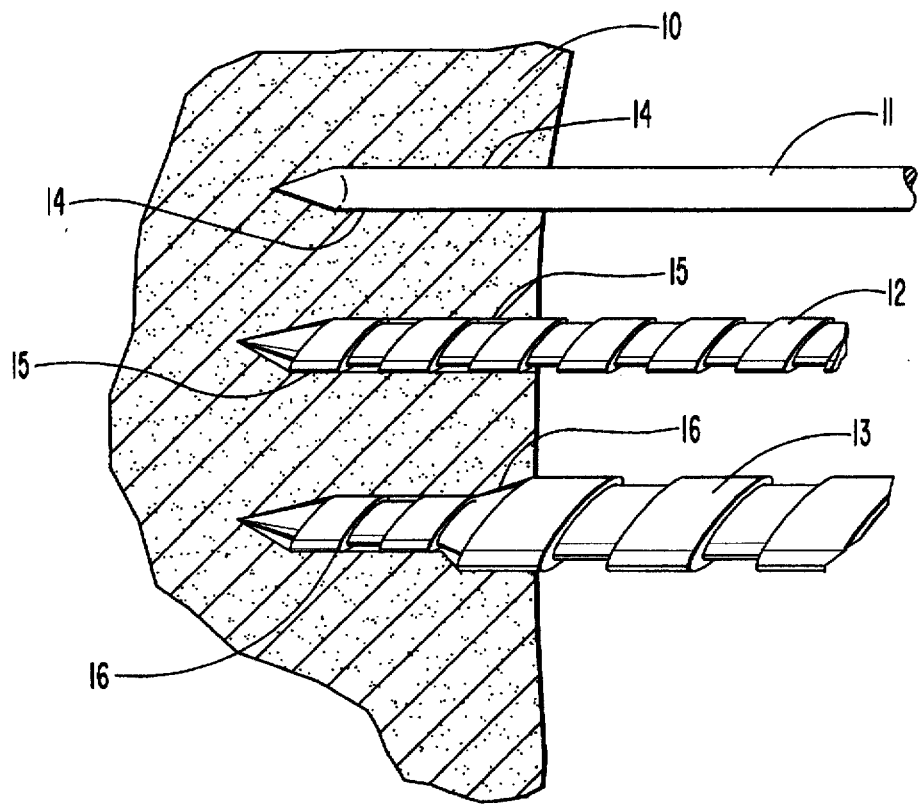
FIG. 1 is a side elevation view of a section of bone showing straight holes formed into the bone cortex utilizing an awl or k-wire, twist drill and twist drill with a countersinking collar.
Figure 2:
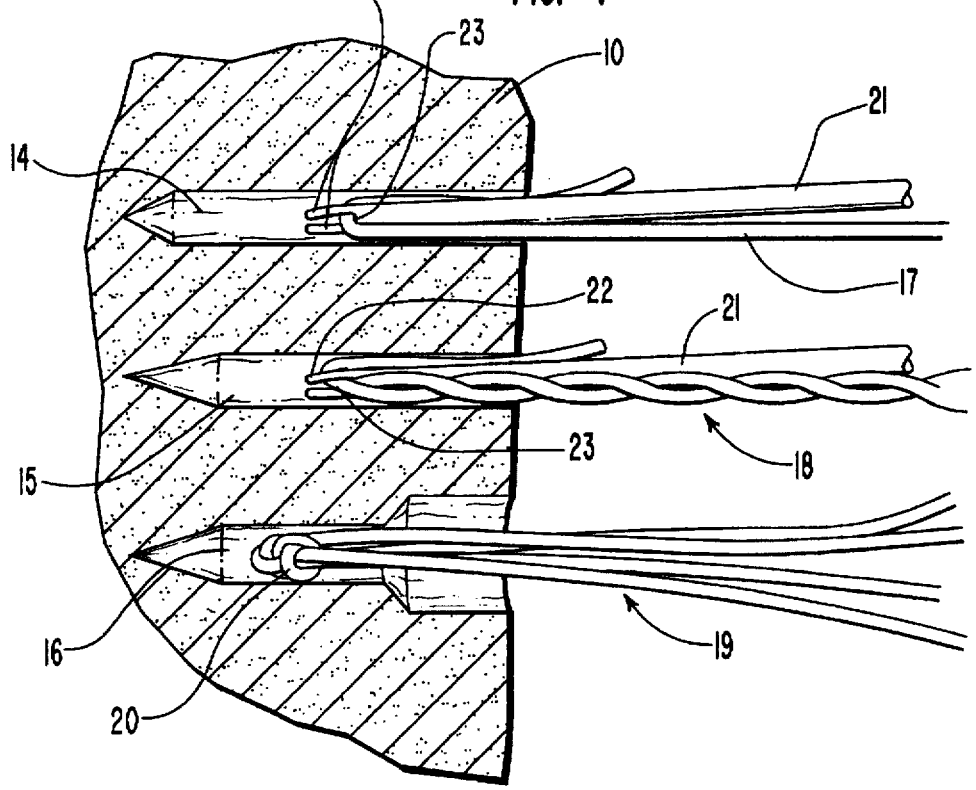
FIG. 2 is a view like that of FIG. 1, with the formed holes shown as receiving a tool fitted therein whereover are positioned single suture, plurality of sutures and a plurality of sutures knotted together.

FIGS. 1, 2 and 3 show a side elevation view of a section of bone material 10 wherein, as shown in FIG. 1, holes are formed into the bone material as by utilizing an awl or k-wire 11, turning a twist drill 12 and twist drill with countersinking collar 13, forming straight holes 14, 15 and 16, respectively. FIG. 2 shows the holes 14, 15 and 16 as having received, respectively, a straight suture 17, a pair of sutures 18 twisted together and a pair of sutures 19 that have a knot 20 tied therein. The single and twisted pair of sutures 17 and 18, respectively, are shown fitted into the respective holes 14 and 15 by folding forward sections of each over an end of a straight insertion rod 21. Which insertion rod includes parallel forward end sections 22 with a space or gap 23 therebetween wherein the suture or sutures are maintained. After, the insertion rod 21 is withdrawn, the folds of the suture 17 and sutures 18 remain in the holes 14 and 15, as shown in FIG. 3. Shown in FIG. 2 the sutures 19 are folded back upon themselves at knot 20, providing sufficient rigidity to allow the suture knot to be slid by an operator into the hole 16.

With the respective suture 17, sutures 18 and knot 20 of sutures 19 fitted into the prepared holes 14, 15 and 16, shown in FIG. 2, and after removal of insertion rod 21, the holes 14, 15 and 16 are filled with an adhesive 24, as shown in FIG. 3. The adhesive is selected to provide, after curing, for maintaining the suture or sutures in the holes 14, 15 and 16, respectively, to withstand a tensile stress as it is anticipated will be exerted thereon. Which tensile stress is at least a stress as would be exerted on the mounting when the suture or sutures are used to connect a ligament, tendon or soft tissue onto the bone surface, or a like use. In practice, to provide which desired pullout strength or purchase, adhesive 24 is selected to be both easily applied and quick curing. An adhesive known as polymethlymethacrylate (PMMA), has been used successively for practicing this procedure, though, it should be understood, the invention is not limited to use of such material and any adhesive material as is suitable for implantation in a human body, such as a grout filling, other adhesive, bone paste, bone plug, light activated resin as used in dental procedures, or the like, can be so used within the scope of this disclosure.

Figure 7A:
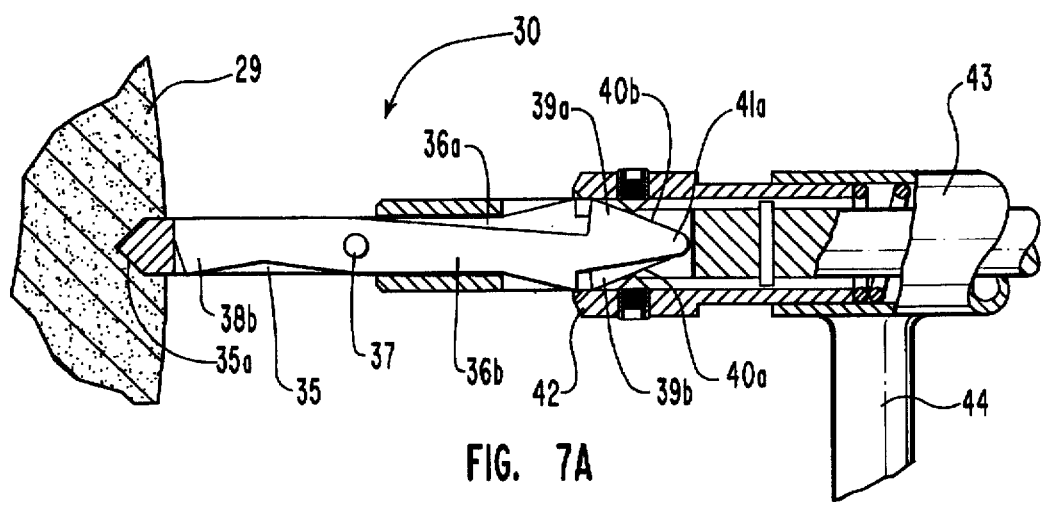
FIG. 7A is a side elevation view of a scissoring twist drill shown drilling a straight hole into a section of bone material.
Figure 7B:
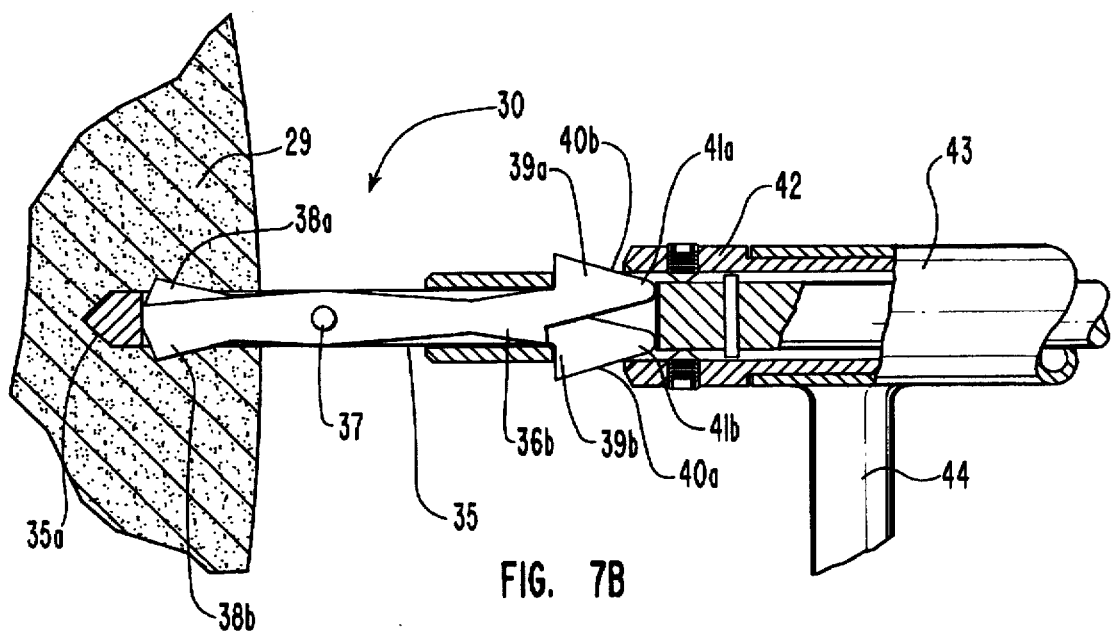
FIG. 7B is a view like that of FIG. 7A except a collar portion of the scissoring twist drill is shown as having traveled upwardly along a drill shaft with the upper ends of reaming arms of the drill shown scissoring outwardly and skirt cutting elements of the drill shown extending outwardly to form a hole in the bone material that has an outwardly flared interior wall.
Figure 7C:
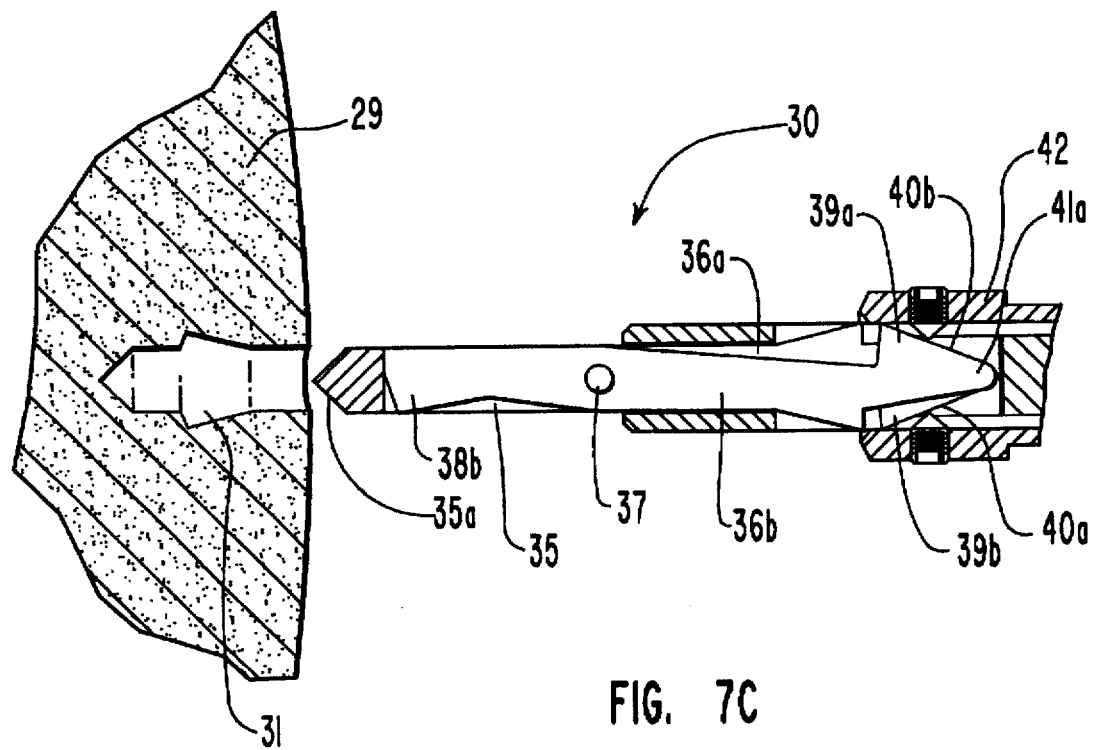
FIG. 7C is a view like that of FIG. 7B with the collar shown returned to the attitude shown in FIG. 7A, closing the reaming arms showing the scissoring twist drill being pulled out of the formed hole.
Figure 8:
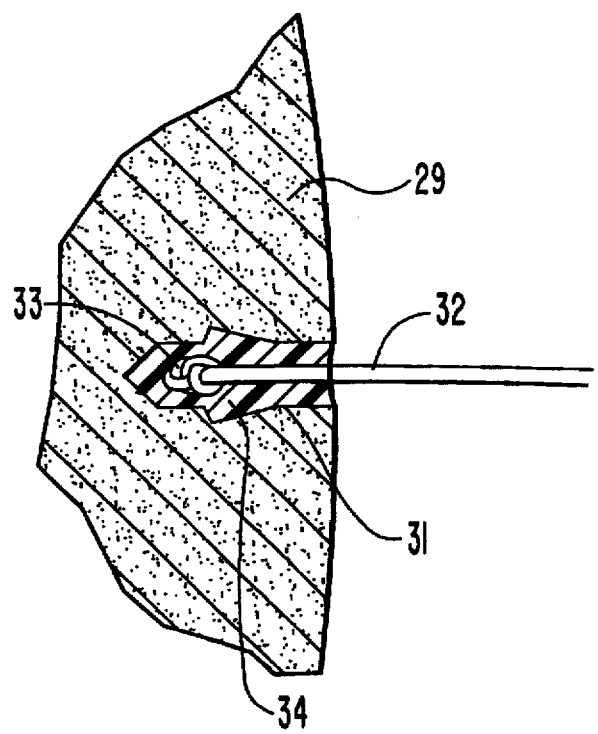
FIG. 8 is a view of the hole formed in the bone material utilizing the scissoring twist drill of FIGS. 7A, 7B and 7C, showing a knotted end of a single suture positioned therein and showing the hole filled with an adhesive.

FIGS. 7A, 7B and 7C show a scissoring twist drill 30 as an example of a device for use for forming an inwardly flared or skirt shaped hole 31 in a bone material 29, as shown in FIG. 8. The hole 31, like the above described holes 14, 15 and 16, is to receive a suture or sutures, shown as a single suture 32 in FIG. 8. The suture 32 can, but is not required to have, a knot 33 tied in an end thereof, or the like, and is fitted in the hole 31 to receive an adhesive 34 therearound that fills hole 31 and, when cured, secures the suture 32 in the bone material 29.

The scissoring twist drill 30, shown in use in FIGS. 7A, 7B and 7C, as set out herein, is an example of a drill type device for forming an inverted counter bore or skirt shaped hole 31 for use as set out above. It should, however, be understood that other arrangements for forming a hole like hole 31 into bone material 29 could be so used within the scope of this disclosure. To provide for drilling the hole 31 the scissoring twist drill 30 is for fitting in and being turned by a conventional drill, or the like.

As shown, the scissoring twist drill 30 includes a straight center shaft 35 therethrough that ends in a twist drill end 35a and is for turning, as shown, into bone material 29. Above the twist drill end 35a, a pair of scissor blades 36a and 36b are mounted to the straight center shaft 35 at pivot 37 to scissor apart. In which blade scissoring, lower cutting ends 38a and 38b and upper camming ends 39a and 39b of the respective scissor blades 36a and 36b spread apart and extend out from and are to be retracted back into the straight center shaft 35. Which scissoring action provides for moving the cutting ends 38a and 38b outwardly to the attitude shown in FIG. 7B. The extended cutting ends of the turning drill 30 ream the hole 31 walls of to the shape shown in FIGS. 7B, 7C and 8, when the camming ends 39a and 39b are spread apart. With, when the camming blades are moved together, as shown in FIGS. 7A and 7C, the cutting ends 38a and 38b are retracted into the straight shaft 35. To provide for which camming blades travel, the camming blades each include an outwardly slopping surface 40a and 40b, respectively, from a narrow rounded top end 41a and 41b, to an inwardly stepped section, respectively. The camming blades top ends 41a and 41b maintain the scissoring blades in a retracted attitude shown in FIGS. 7A and 7C, so long as a first sleeve 42 is fitted thereover. The sleeve 42 is preferably biased by a spring, not shown, to resist positioning over the camming blade top ends. To extend or outwardly pivot the scissoring blades cutting ends 38a and 38b, to the altitude shown in FIG. 7B, a second sleeve 43 is journaled to the straight shaft to remain stationary as the straight shaft is turned and, engages the first sleeve 42 that moves over the camming blade top ends 41a and 41b, as shown in FIGS. 7A and 7C. To control which second sleeve 43, a handle 44 is fitted to extend out from the second sleeve surface to be held by an operator, who manually retracts the first sleeve 42 telescoping into the second sleeve 43, allowing the camming ends 38a and 38b to spread apart as shown in FIG. 7B.

In practice, for forming hole 31, an operator holding the handle 44 in one hand and the sleeve 42 in their other, as shown in FIG. 7A and drills into the bone material 29. At a desired depth, the operator holding on the handle 44, pulls the first sleeve 42 into the second sleeve 43 allowing the scissoring blades camming ends 39a and 39b to move outwardly that also pivot the scissoring blade cutting ends 38a and 38b outwardly. The cutting ends are thereby moved the attitude shown in FIG. 7B, reaming out the hole 31 to have an inverted counterbore or skirted top portion, as shown best in FIG. 8. Thereafter, to remove the twist drill after hole 31 is formed, holding handle 44, the first sleeve 42 is moved out of the second sleeve 43, traveling over the scissor blade camming ends 39a and 39b, to pivot the scissoring blades 36a and 36b back into the straight shaft 35. With the scissoring blades retracted, as shown in FIG. 7C, the twist drill 30 drill end 35a can be pulled out of the formed hole 31. Which hole 31 then receives, as set out above, a suture end portion and an adhesive to mount that suture end portion in the hole 31 in bone material 29.

FIGS. 4, 5 and 6 are here provided to illustrate a relationship between suture configuration and hole dimensions for providing a required purchase of the suture that is mounted to the bone material of the invention. In practice, where a suture is to be used for securing a tendon, ligament, or the like, onto a bone surface, a pull out strength greater than the yield strength of the suture is preferred. Which purchase is a function of the adhesive properties of a selected adhesive 52, the surface area of the wall of a hole formed into the bone and the surface area of the portion of a suture or sutures fitted in the hole that is covered by the adhesive after curing. FIG. 4 illustrates how a shallow hole 51 formed into bone material 50 can provide a required purchase to a plurality of sutures that have been tied into a knot that is arranged in the hole 51. For the suture mounting of FIG. 4, an adhesive material 52, like that set out above as adhesive 24 known as polymethlymethacrylate or crnoacralate, light activated resin, or the like, can be used. To compute the purchase as will be obtained for this adhesive 52 the hole 51 is formed to have a diameter, shown as d, and height h, to provide a wall area (Aw) having a surface area that is greater than or equal to the suture surface area (As) of the portion of the suture that is in the hole. To provide a required purchase or pullout strength. For FIG. 4, the suture surface area (As) is the combined thickness of sutures 53 and further includes, at least the surface area of a knot 54 (Ak) computed utilizing the knot 54 diameter Kd. Which knot 54 has been tied in the sutures 53. The knot 54, in practice, effects a column of the cured adhesive 52 and thereby is believed to further increases purchase over the purchase obtained considering the suture and knot surface areas alone.

To further illustrate a relationship between the hole dimensions and suture or sutures, FIG. 5 shows a single suture 56 positioned in a hole 55 that is narrower, shown as diameter d, with a greater height, shown as h, than the hole 51 of FIG. 4. A knot 57 is shown tied in the suture 56 end for further increasing purchase. For calculating purchase of the suture 56 in the hole 55, after curing of adhesive 52 therein, the hole area in relation to the suture and knot surface areas are considered, as set out above, with the presence of knot 57 increasing purchase.

The relationship of hole wall surface area and the suture surface area, as set out above, is taken into consideration to provide at least a required purchase using an adhesive 52, as shown in FIG. 6. Shown therein, a narrow hole 58, shown as having a diameter d, and has a greater height, h, than the height of holes 51 and 55 of FIGS. 4 and 5, is provided for mounting a single suture 59 therein. Which suture 59, as shown, does not have a knot, or the like, formed in the end thereof. So arranged, as the suture 59 lacks a knot, additional purchase as such knot would provide is not available, and the purchase is calculated from the relationship of the hole wall area and suture surface area only.

While preferred embodiments of the present invention in a suture mounting system and process have been shown and described herein, it should be apparent that this disclosure is made by way of example only and that variations to both the suture mountings and processes are possible within the scope of this disclosure without departing from the subject matter coming within the scope of the following claims and a reasonable equivalency thereof, which claims we regard as our invention.

We claim:

1. A process for anchoring at least one suture to a bone section consisting of, forming a hole into a bone, with said hole having a diameter and formed to a depth to provide an inner wall surface area that is at a minimum slightly greater than the surface area of an end section of a suture to be fitted therein; positioning an end section of at least one suture in said formed hole; and filling said suture containing hole with an adhesive material.

2. A process as recited in claim 1, further including forming the hole into a bone material to have an outwardly sloping portion.

3. A process as recited in claim 1, wherein the adhesive material is a biocompatible bone cement, resin cyanoacrylate.

4. A process as recited in claim 1, where the adhesive material is a grout, filling adhesive, bone paste, bone plug, or light activated resin material suitable for implantation in a human body.

5. A process for anchoring at least one suture to a bone section as recited in claim 1, further including fitting the suture end section axially into the hole and said suture end section forms approximately a right angle to a top surface of said adhesive material.

* * * * *